US008452064B2

(12) United States Patent
Ross et al.

(10) Patent No.: US 8,452,064 B2
(45) Date of Patent: May 28, 2013

(54) APPARATUS AND METHODS FOR GEOMETRIC CALIBRATION OF POSITRON EMISSION TOMOGRAPHY SYSTEMS

(75) Inventors: Steven Gerard Ross, Pewaukee, WI (US); Timothy Deller, Pewauke, WI (US); Charles William Stearns, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 783 days.

(21) Appl. No.: 12/632,393

(22) Filed: Dec. 7, 2009

(65) Prior Publication Data

US 2011/0135179 A1 Jun. 9, 2011

(51) Int. Cl.
*G06K 9/36* (2006.01)

(52) U.S. Cl.
USPC .......................................... 382/131

(58) Field of Classification Search
None
See application file for complete search history.

(56) References Cited

U.S. PATENT DOCUMENTS

| 5,872,829 | A | * | 2/1999 | Wischmann et al. | 378/164 |
|---|---|---|---|---|---|
| 6,130,958 | A | * | 10/2000 | Rohler et al. | 382/131 |
| 8,189,889 | B2 | * | 5/2012 | Pearlstein et al. | 382/128 |
| 2007/0176087 | A1 | * | 8/2007 | Wang et al. | 250/252.1 |
| 2009/0314933 | A1 | * | 12/2009 | Breuer et al. | 250/252.1 |
| 2009/0316972 | A1 | * | 12/2009 | Borenstein et al. | 382/131 |
| 2010/0195804 | A1 | * | 8/2010 | Dafni et al. | 378/207 |
| 2011/0127413 | A1 | * | 6/2011 | Casey et al. | 250/252.1 |
| 2011/0249879 | A1 | * | 10/2011 | Wu et al. | 382/131 |

OTHER PUBLICATIONS

Bailey et al., An Investigation of Factors Affecting Detector and Geometric Corrrection in Normalisation of 3D PET Data, IEEE Trans. Nucl. Sci. 43(6), 3300-3307.

Oakes et al., Normalization for 3D PET with a low-scatter planar source and measured geometric factors, Phys. Med. Biol. 43 (1998) 961-972, Printed in the UK.

B Bai et al., Model-based normalization for iterative 3D PET image reconstruction, Phys. Med. Biol. 47 (2002) 2773-2784, Printed in the UK.

* cited by examiner

*Primary Examiner* — Brian P Werner

(74) *Attorney, Agent, or Firm* — The Small Patent Law Group; Dean D. Small

(57) ABSTRACT

Apparatus and methods for geometric calibration of positron emission tomography (PET) systems are provided. One method includes obtaining scan data for a uniform phantom and generating reference images based on the scan data for the uniform phantom. The method further includes reconstructing images of the uniform phantom using a PET imaging system and determining a geometric calibration for the PET imaging system based on a comparison of the reconstructed images and the reference images.

22 Claims, 5 Drawing Sheets

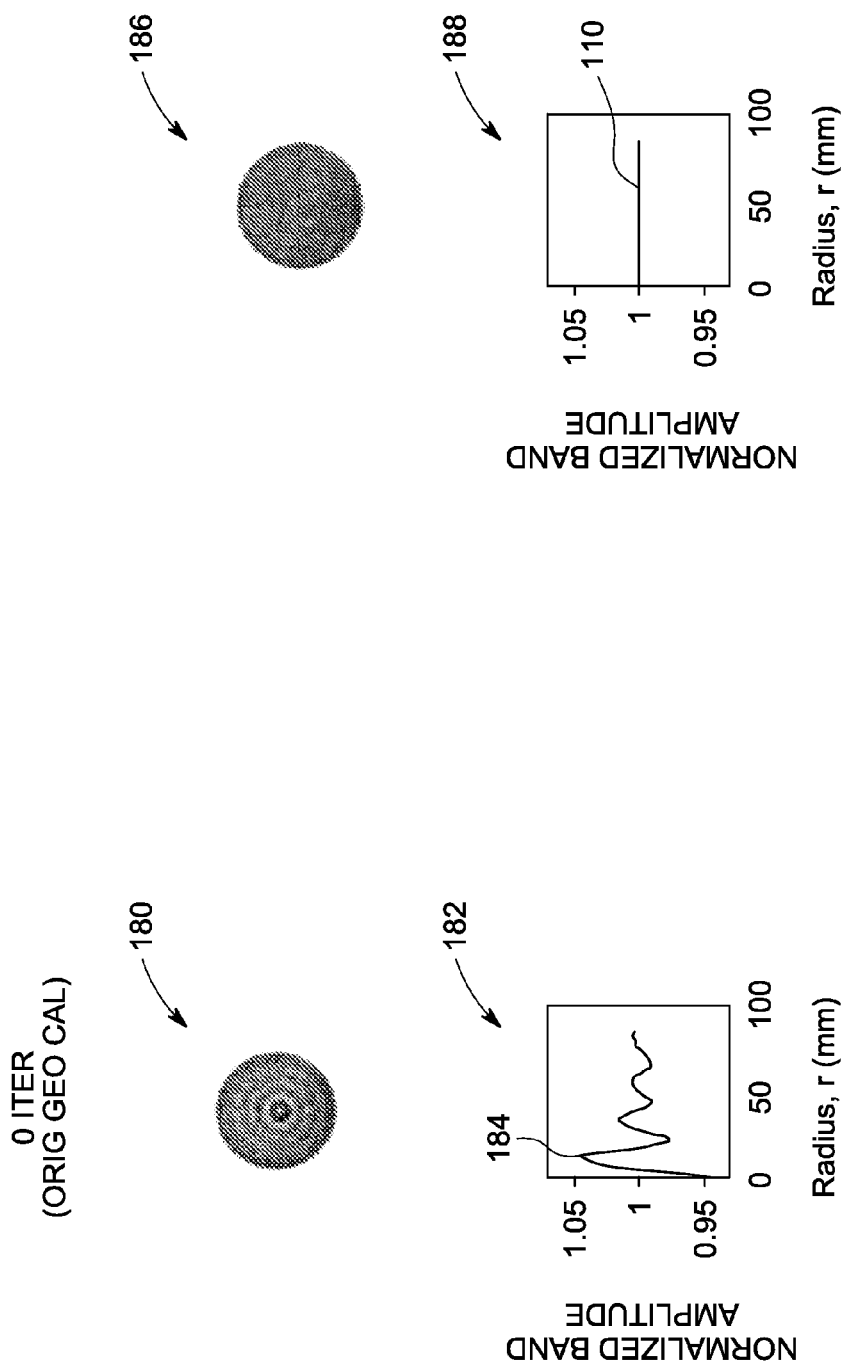

APPARATUS AND METHODS FOR GEOMETRIC CALIBRATION OF POSITRON EMISSION TOMOGRAPHY SYSTEMS

BACKGROUND OF THE INVENTION

The subject matter disclosed herein relates generally to diagnostic imaging systems, and more particularly to positron emission tomography (PET) imaging systems and geometric calibration of the PET imaging systems.

PET imaging systems typically generate images depicting the distribution of positron-emitting nuclides in patients based on coincidence emission events detected using a detector system, usually configured as a detector ring assembly of detector blocks. In PET image reconstruction, data corrections are implemented that account for the geometric properties of the detector system. For example, the angle between two detector faces affects the number of coincidence emissions measured. Additionally, the physical design and alignment of the detector blocks also include geometric variances, such as the location of a crystal within a detector block. Moreover, manufacturing tolerances affect the physical alignment of each PET system differently, including the PET detector crystals and photomultiplier tubes.

The differences in materials and manufacturing processes, thus, affect the geometric calibration measurement and resulting correction coefficients for these PET systems. If the system geometry is not accounted for during image reconstruction, then image artifacts can appear. These artifacts include "bands" (also referred to as "rings"). For example, bands in axial slice images appear as streaks in reformatted coronal and sagittal images. Additionally, inconsistencies at the image center, such as "divots", can also occur.

Conventional methods measure and obtain corrections for these geometric variations. For example, some conventional calibration methods to perform geometric correction acquire a scan of a rotating pin source at the outside of the PET field of view (FOV), which allows measurement of coincidence pairs for every line of response (LOR) for the system. However, because the pin source is of a finite radius, acquisition of an ideal line source is prevented. Additionally, acquisition imperfections from detector dead time issues can affect the data. Also, because the pin rotates very close to the detector faces, the detectors near the pin can become overloaded with counts, increasing the dead time and degrading the quality of the resulting geometric calibration.

BRIEF DESCRIPTION OF THE INVENTION

In accordance with various embodiments, a method for providing geometric calibration for a positron emission tomography (PET) imaging system is provided. The method includes obtaining scan data for a uniform phantom and generating reference images based on the scan data for the uniform phantom. The method further includes reconstructing images of the uniform phantom using a PET imaging system and determining a geometric calibration for the PET imaging system based on a comparison of the reconstructed images and the reference images.

In accordance with other embodiments, a computer readable medium for calibrating a positron emission tomography (PET) imaging system is provided. The computer readable medium is programmed to instruct a computer to generate artifact reduced PET reference images based on a priori information of a scanned uniform phantom. The computer readable medium is further programmed to instruct the computer to determine a geometric calibration for the PET imaging system using an image-domain based iterative calibration determination process with image-based feedback from the reference images.

In accordance with yet other embodiments, a positron emission tomography (PET) imaging system is provided that includes a gantry and a detector ring mounted to the gantry, with the detector ring having a plurality of detector elements. The PET imaging system further includes a geometric calibration determination module configured to generate reconstructed images of a uniform phantom imaged by the plurality of detector elements to create a plurality of reference images used in an iterative image-based feedback process and to determine a geometric calibration for the imaging detectors.

BRIEF DESCRIPTION OF THE DRAWINGS

FIG. 3 is a diagram illustrating image banding and a corresponding normalized band amplitude plot.

FIG. 4 is a diagram illustrating a reference image without banding formed in accordance with various embodiments and a corresponding normalized band amplitude plot.

DETAILED DESCRIPTION OF THE INVENTION

Figure 1:
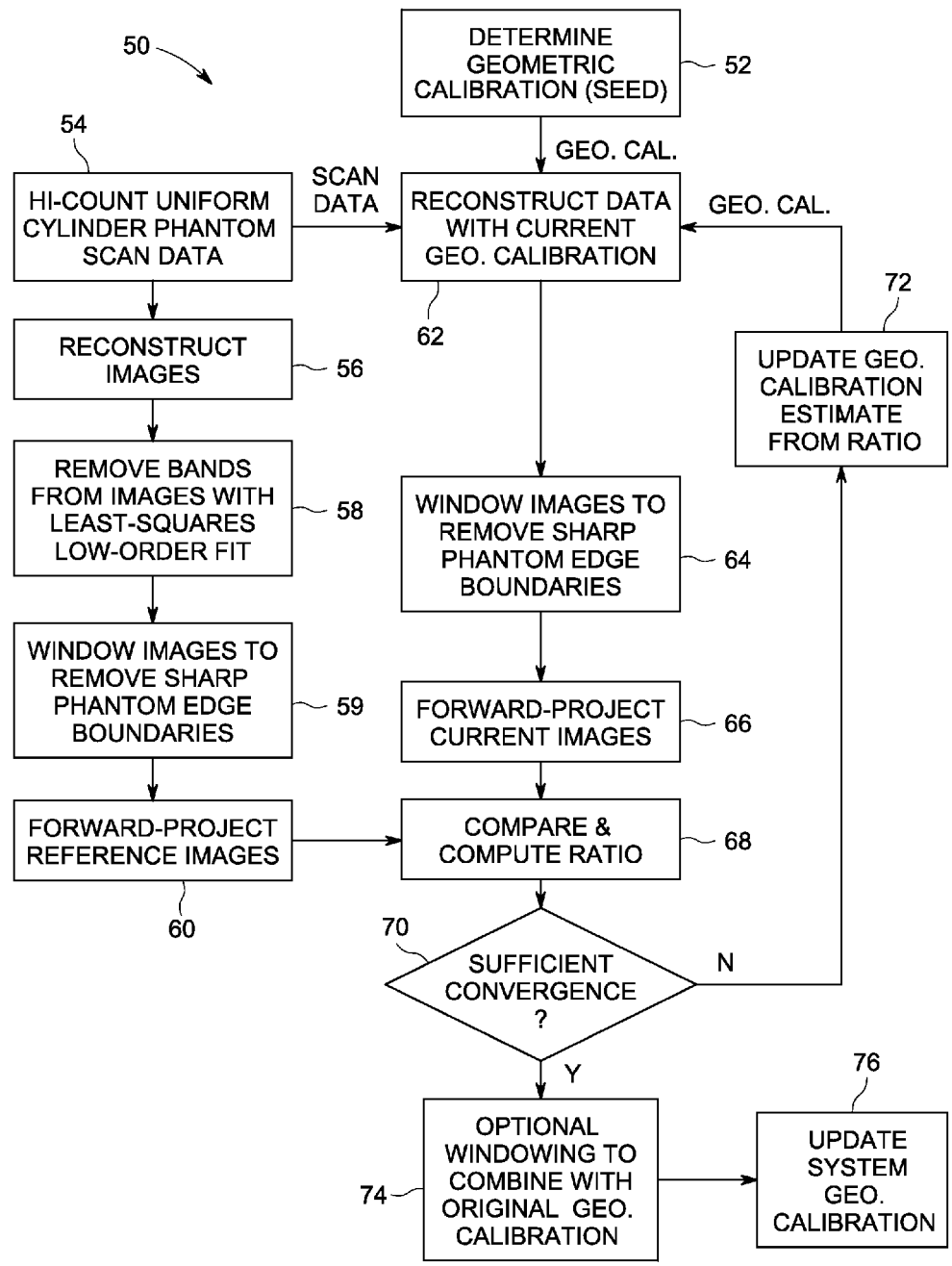
FIG. 1 is a flowchart of a method for providing geometric calibration of positron emission tomography (PET) imaging systems in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide an image-domain based method for geometric calibration of positron emission tomography (PET) systems. Using iterative feedback from reconstructed images, geometric coefficients for system or scanner calibration are determined. The geometric coefficients may be used to calibrate a group of PET systems or individual PET systems. At least one technical effect of the various embodiments is the reconstruction of images having reduced image artifacts. For example, image banding in reconstructed images may be reduced in accordance with various embodiments. Thus, reconstructed images are more accurate and uniform because, rings/bands, hot-spots and cold-spots are reduced or removed from reconstructed images. Reduction or elimination of artifacts improves diagnostic ability by reducing distractions in the images. Moreover, additional calibration equipment is not needed to perform the geometric calibration of the various embodiments. Moreover, the geometric calibration of the various embodiments may be performed multiple times or on a regular calibration schedule at, for example, a clinical site.

The various embodiments are implemented in connection with a PET system, which in some embodiments includes computed tomography (CT) imaging capabilities, for example, configured as a multi-modality imaging system, such as a PET/CT imaging system. However, it should be appreciated that although the various embodiments are described in connection with a PET/CT imaging system having a particular configuration, the various embodiments may be implemented in connection with PET/CT imaging systems have different configurations and components, as well as with other types of dual-modality imaging systems, for example, a single photon emission computed tomography (SPECT)/CT imaging system. Other modalities may be used, for example, an ultrasound system, Magnetic Resonance Imaging (MRI) or any other system capable of generating physiological activity distribution images and/or tomographic images. Moreover, the imaging detectors may be of different types and configurations. Also, although the various embodiments are described in connection with a multi-modality imaging system, the various embodiments may be implemented in a one or more single modality imaging systems.

In accordance with various embodiments, a method 50 for providing geometric calibration of PET imaging systems is shown in FIG. 1. In particular, the method 50 in some embodiments includes an iterative process that may be used with an existing geometric calibration seed, for example, to improve an existing geometric calibration. Specifically, the method 50 includes initially determining a geometric calibration seed at 52 (e.g., geometric calibration estimate), which may be or may have been previously determined using any suitable geometric calibration method in the art. It should be noted that the seed may be defined by predetermined geometric calibration coefficients determined and generated from a geometric calibration estimate process in the art. For example, methods may be used that generate geometric calibration coefficients for the geometry of a particular PET imaging system. As used herein, geometric calibration coefficients refers to any values, which may be, for example, scalers or variables that are used to compensate or correct for geometric differences or variations within a single PET imaging detector (e.g., differences between different imaging blocks) or among a number of PET imaging detectors.

Thereafter a uniform flood phantom scan is acquired at 54 using a PET imaging scanner or system. Additionally, attenuation correction information, for example, from an x-ray CT scan also may be acquired. The uniform flood phantom may be a uniform cylinder phantom, such as a radioactive cylinder having a constant radioactive activity level and in various embodiments is a centered phantom, namely placed in the center of imaging scanner, such as centered or centrally within a bore of the imaging scanner. The uniform flood phantom can be used to generally measure the uniformity and sensitivity of the PET imaging system. In general, the uniform flood phantom can be any radioactive phantom that produces a generally flat and homogeneous image when scanned. In various embodiments, the scan at 54 results in high-count (namely, high photon count) uniform cylinder phantom data.

Figure 2:
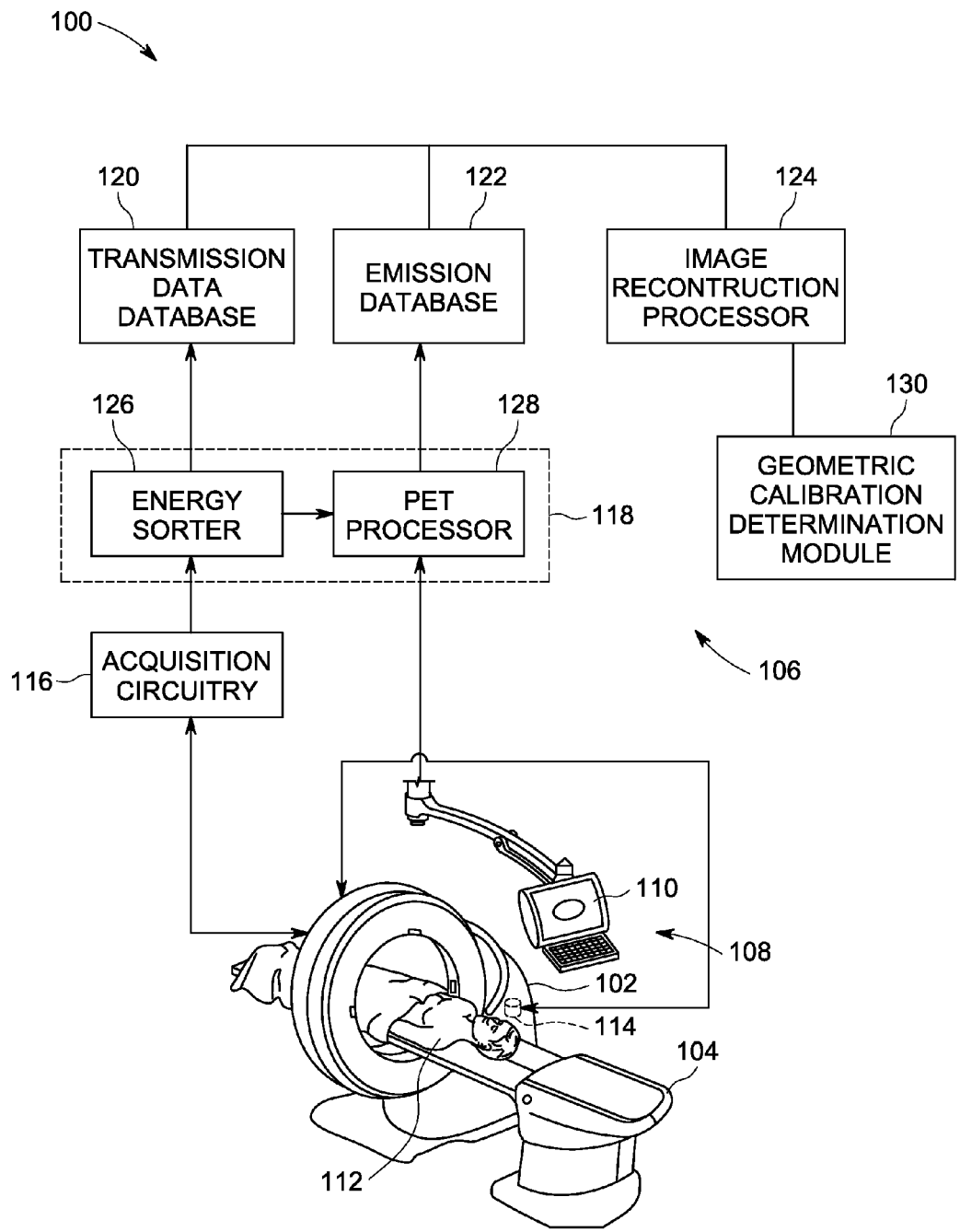
FIG. 2 is a schematic block diagram illustrating a positron emission tomography/computed tomography (PET/CT) dual imaging system formed in accordance with various embodiments.

The flood phantom scan and x-ray CT imaging scan may be performed using a PET/CT imaging system 100 as illustrated in FIG. 2. In some embodiments, the scan information and the steps of the method 50 are performed using a plurality of different imaging systems, and in other embodiments, using a single imaging system. It should be noted that in some embodiments, the CT data is acquired prior to obtaining the PET data. However, the data may be acquired in different orders and combinations thereof (e.g., in an interleaved manner).

The medical imaging system, such as the PET/CT imaging system 100, generally includes a gantry 102, a patient table 104, and a processing and control system 106 including a user input 108 with a display 110. The gantry 102 provides mechanical support for imaging devices such as, for example, detectors, scanners and transmitters that are used for scanning a phantom or patient. The gantry 102 houses imaging devices such as, for example, PET detectors or x-ray detectors. It should be noted that the PET system may be a stationary annular detector or optionally may include a pin source, which may be used to acquire the seed estimate at 52 of the method 50 (shown in FIG. 1).

The imaging devices on the gantry 102 acquire image data by scanning a phantom or patient on the patient table 104. Moving the patient table 104 enables the scanning of various portions of the phantom or patient. The patient table 104 lies along the axis of gantry 102, which is known as a viewing area along an examination axis and can be moved along this axis. The patient table 104 can be positioned at various axial positions along the axis. In some embodiments, the gantry 102 includes a plurality of PET detectors that are fixed and spaced on gantry 102, which are positioned radially outward from the axis and that may be configured as one or more rings of detectors. In accordance with other embodiments, the gantry 102 includes a plurality of detectors that are rotatable about the axis. For CT imaging, such as to acquire attenuation correction information, a rotating detector and a source, for example, an x-ray tube 114 may be provided and optionally a stationary detector ring for CT imaging may be provided. In other embodiments, a separate imaging gantry is provided for CT imaging.

The processing and control system 106 controls the positioning of the patient table 104, as well as receiving calibration and image data collected during scanning. In various embodiments, the processing and control system 106 controls the medical imaging system 100 to acquire both phantom scan information, image information and/or attenuation correction information of a volume of interest, for example, a uniform flood phantom or patient and as described in more detail herein. For example, annihilation events may be detected as emission data from the uniform flood phantom, as well as transmission data from signals transmitted by a transmission source, such as the x-ray tube 114, which pass through the volume of interest. The transmission signals are attenuated when the signals pass through the volume of interest and the detectors collect data that is attenuated after the transmission signals pass through volume of interest.

Various processors, sorters, and databases are used to acquire and manipulate emission and transmission data, which is used in accordance with various embodiments. The processors, sorters and databases of FIG. 2 include acquisition circuitry 116, an acquisition processor 118, a transmission data database 120, an emission database 122, and an image reconstruction processor 124. The acquisition processor 118 is programmed to acquire emission data, for example, in a list mode and/or a sinogram mode, as described in more detail below, and generate an image based on the emission data acquired in the list mode and/or the emission data acquired in the sinogram mode. Iterative feedback from reconstructed images are used in the image-domain based geometric calibration method 50 of FIG. 1. The medical imaging system 100 may also include other computing components.

In some embodiments, an energy sorter 126 provides, for example, time, location, and energy data to a PET processor 128. The PET processor 128 generally uses the received data to identify pairs of data, also known as coincidence pairs, coincident pair lines and lines of response, corresponding to annihilation events that occurred inside the region of interest. After acquisition processor 118 identifies an annihilation event, the acquisition processor 118 updates data in the emission data database 122 to store information relating to the annihilation events. X-ray CT data is also stored in the transmission data database 120 based on transmission signals that pass through the volume of interest (e.g., phantom) and are detected.

Thus, after an acquisition session has been completed and sets of transmission and emission data have been stored in databases 120 and 122, respectively, image reconstruction processor 124 accesses the data in the databases 120 and 122 and uses the accessed data to generate images that may be requested by a system operator. Additionally, the sets of transmission and emission data are used by a geometric calibration determination module 130 to perform geometric calibration determination in an image-domain based process as described in more detail herein.

Referring again to the method 50 of FIG. 1, the phantom scan data is reconstructed into images at 56. The reconstruction of the emission data may be performed in any suitable manner using any type of image reconstruction process, such as analytical image reconstruction algorithms known in the art. The images are reconstructed from the scan of the uniform flood phantom and using the geometric calibration estimate seed determined at 52. Accordingly, PET images are reconstructed using the seed geometric calibration to compensate for geometric variations. In some embodiments, the images are reconstructed without any geometric calibration applied thereto. The PET images show photon activity distribution within the phantom and which may be reconstructed from emission sinograms. The reconstructed PET images should appear flat with no ripples or bands because the flood phantom has a uniform radioactive activity distribution. However, as illustrated in FIG. 3, the reconstructed images 180 (one image is shown) may include a plurality of bands that cause image artifacts. The reconstructed image 180 shown is a summed image in the z-direction of the uniform flood phantom. The graph 182 illustrates a corresponding plot 184 of the normalized band amplitude versus radius for the reconstructed image 180 showing the ripples that cause the banding artifacts.

Referring again to the method 50 of FIG. 1, the image artifacts (e.g., image bands) in the reconstructed image 180 are removed at 58. In particular, using a priori knowledge that the imaged phantom is uniform in photon activity distribution, the displayed bands are removed from the image in the image domain. For example, the photon counts associated with the banding in the reconstructed image 180 are adjusted to compensate for and remove the bands from the reconstructed image 180. Accordingly, a reference image 186 as shown FIG. 4 is generated that is band-free such that the photon distribution uniformity is provided as illustrated by the graph 188 showing the flat line corresponding plot 190 of the normalized band amplitude versus radius.

Any suitable method may be used to remove the bands from the reconstructed image 180 and ensure uniformity, for example, a low order (e.g., a second order) least squares surface fit. In some embodiments, the phantom image may be replaced with an average of the phantom image. Generating the reference image 186 in this manner provides an image with reduced or eliminated artifacts, such as reduced or eliminated bands in the image or reduced or eliminated inconsistent pixel values at the location corresponding to the center of the PET gantry. In various embodiments, one or more reference images 186 are used by the method 50 to modify or adjust the original geometric calibration (seed calibration) to reduce or minimize image artifacts.

Referring again to the method 50, thereafter windowing may optionally be performed at 59 to reduce or eliminate boundary limitations from the phantom. For example, a windowing process may be performed using any suitable method to remove sharp phantom edge boundaries. In some embodiments, thresholding may be used to smooth imaged edges of the phantom, for example, as a result of the phantom being smaller than the bore. In some embodiments segmentation methods may be used to identify the boundary and remove sharp edges in the reconstructed images.

Figure 5:
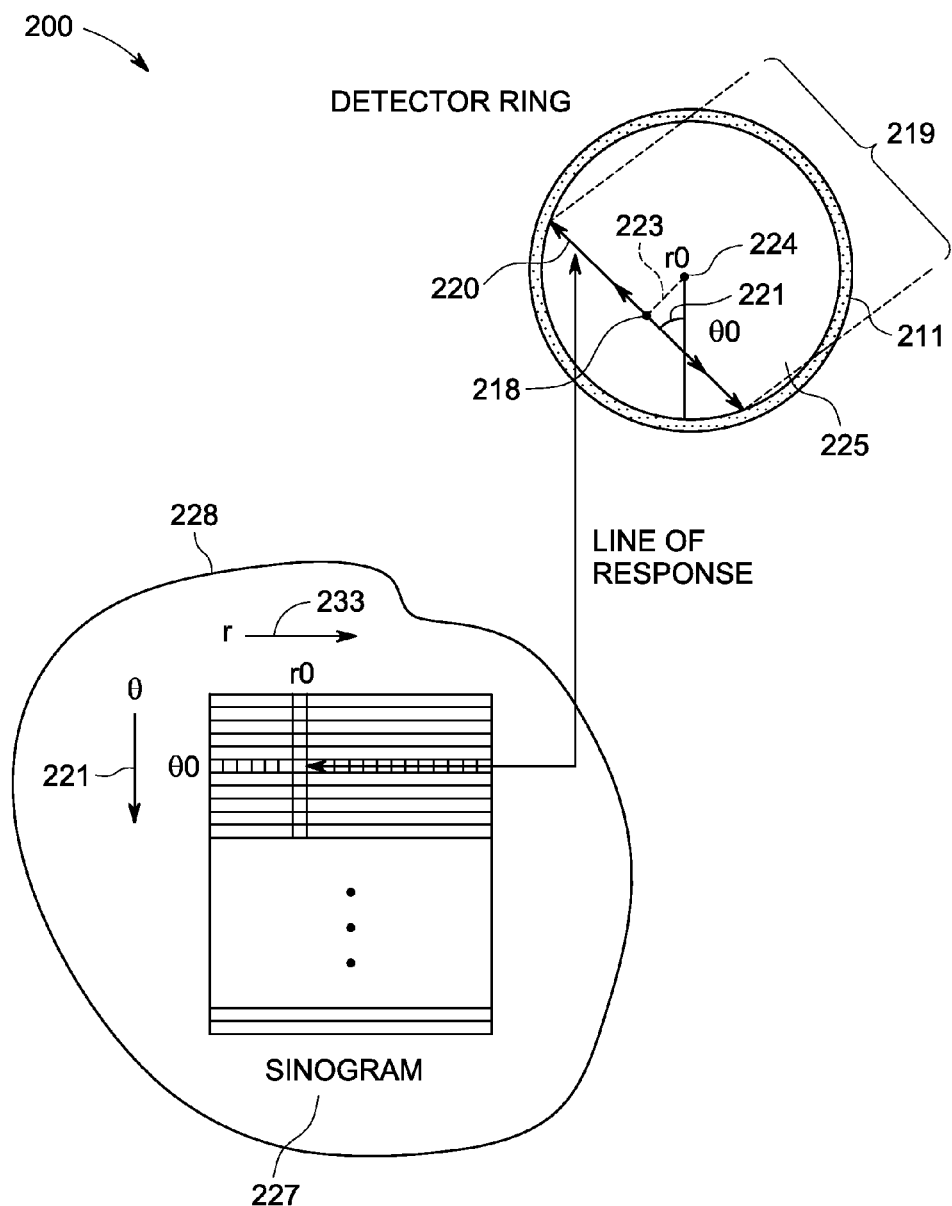
FIG. 5 is a diagram of a detector ring and an illustration of the construction of a sinogram used in various embodiments.

Thereafter the one or more reconstructed reference images 186 are forward-projected at 60. Thus, a reduced band or band-free image set is forward-projected using any suitable forward projection method. For example, as shown in FIG. 5, the energy sorter 126 (shown in FIG. 2) receives a coincidence event pair 219 of an annihilation event 218 and identifies a corresponding line of response 220. Each line of response 220 may be identified by an angle ($\theta$) 221 and a distance (r) 223 from a center 224 of the field of view 225. The array of the responses 220 is known as a sinogram 227, which may be stored as a 2D or 3D distribution. The sinogram 227, which is an emission sinogram, is essentially a histogram of detected coincidence events where each of a plurality of bins in the histogram represents a potential detector pair element. Accordingly, in some embodiments, the one or more reference images 186 are forward projected to map the reduced band or band-free images to the sinogram space.

It should be noted that the imaging system 100 may include multiple rings 211 of detectors covering, for example, 15-25 centimeters in the axial direction. Detectors typically include radiation detectors with sufficiently high timing resolution. The high timing resolution may be required to discriminate between at least two positions along the line of response 220 joining two such detectors. The photons are emitted in opposite directions along the line of response 220 and are detected by detectors placed on the line of response 220.

PET data may be acquired in either a two-dimensional (2D) or three-dimensional (3D) mode. In the 2D acquisition mode, lines of responses 220 occurring in the same ring 211 or immediately adjacent ring 211 are accepted. In the 3D mode, any line of response 220 occurring between any pair of detector rings 211 is acquired. In the 2D mode, the coincident events 219 that are acquired within the same detector ring 211 contribute to the direct planes, while those events 219 across neighboring rings 211 contribute to the cross planes.

Referring again to the method 50, after the one or more reference images 186 are forward projected, the geometric calibration coefficients are updated one or more times as described in more detail below. Accordingly, in various embodiments, an iterative process is performed that updates the geometric calibration coefficients. In general, for each iteration the current geometric calibration is used to reconstruct images that are compared to the reduced band or band-free or artifact-free reference image(s) 186. In particular, PET images, for example of the phantom, are reconstructed with the seed geometric calibration at 62 to generate images, which may be performed in the same manner as described above with respect to the reconstruction at 56. Thus, the reconstructed images include banding or image artifacts in various embodiments. In this iterative loop, windowing may optionally be performed at 64 similar to the windowing performed at 59.

Thereafter, the reconstructed images are forward projected at 66. The forward projection may be performed as described above in connection with step 60. Accordingly, the reconstructed images with the geometric calibration and the reference image(s) 186 are both provided in the projection space. The forward projected images from step 66 is compared to the reference image(s) 186 from step 60 to determine a difference from ring reduced or ring-free or artifact-free images as defined by the reference image(s) 186. Accordingly, a comparison is performed in the projection space to determine a ratio at 68, which is then used to update the geometric calibration, for example, for the next iteration. The calculated ratio may be based on a comparison of sinograms, for example, a comparison of each bin in the sinograms for each location in space (e.g., each coordinate location) for corresponding images (reconstructed images versus reference images 186) to determine the ratio, which may be for each bin or for the overall sinogram. An average or summed ratio may, for example, be determined.

Thereafter, a determination is made at 70 as to whether there is sufficient convergence, such as whether the ratio is within a predetermined percentage of unity (ratio=1). If a determination is made that there is not sufficient convergence, then the geometric calibration estimate is updated at 72 based on the ratio. In various embodiments, the geometric calibration coefficients are modified to result in an image closer to the reference image(s) 186. Thus, the modification of the geometric calibration coefficient attempts to modify a current image to appear more like the reference image(s) 186. The geometric calibration coefficients may be scaled up or down, which scaling may vary based on the location in the detector crystal. For example, the geometric calibration coefficients for the edge of the detector crystal may be weighted more than the middle of the detector crystal, such that the photon counts are scaled up more at the edge or outside region of the detector crystal than the middle region of the detector crystal. For example, in the outside region of the detector crystal, which may be defined as a predetermined distance from the edge, the photon counts may be scaled using an 8 to 12 counts ratio while the middle portion of the crystal may be scaled using a 10 to 12 counts ratio. The geometric calibration coefficients may be defined in any suitable manner, for example, based on the particular PET imaging system.

After the updating of the geometric calibration estimate at 72 the iterative process at steps 62-68 are repeated (applying the new updated or modified geometric calibration), which accordingly includes a comparison of images reconstructed using the modified geometric calibration to the reference image(s) 186. A determination is then made again at 70 as to whether there is sufficient convergence, for example, to an acceptable level, and if not, the iterative process is repeated.

However, if there a determination at 70 that sufficient convergence has occurred, such that any banding or artifacts is within an acceptable level, then an optional windowing process may be performed at 74. The windowing process may be used to combine the newly modified geometric calibration with the original calibration, for example, the seed calibration. The windowing may be performed using any suitable windowing process, for example, by defining a width of analysis windows to use during the combining. Thereafter, the system geometric calibration is updated at 76. For example, the geometric calibration coefficients are updated based on the computed ratio at 68 from the last iteration. Thus, when the convergence of the iterative process at steps 62-72 has satisfied a requisite or predetermined level, the geometric calibration from the last iteration is used to update the PET geometric calibration, which may be used for and/or applied to, for example, PET scanners with the same type of detector geometry, such as the same size, shape and/or configuration of detector rings and detector blocks.

Figure 6:
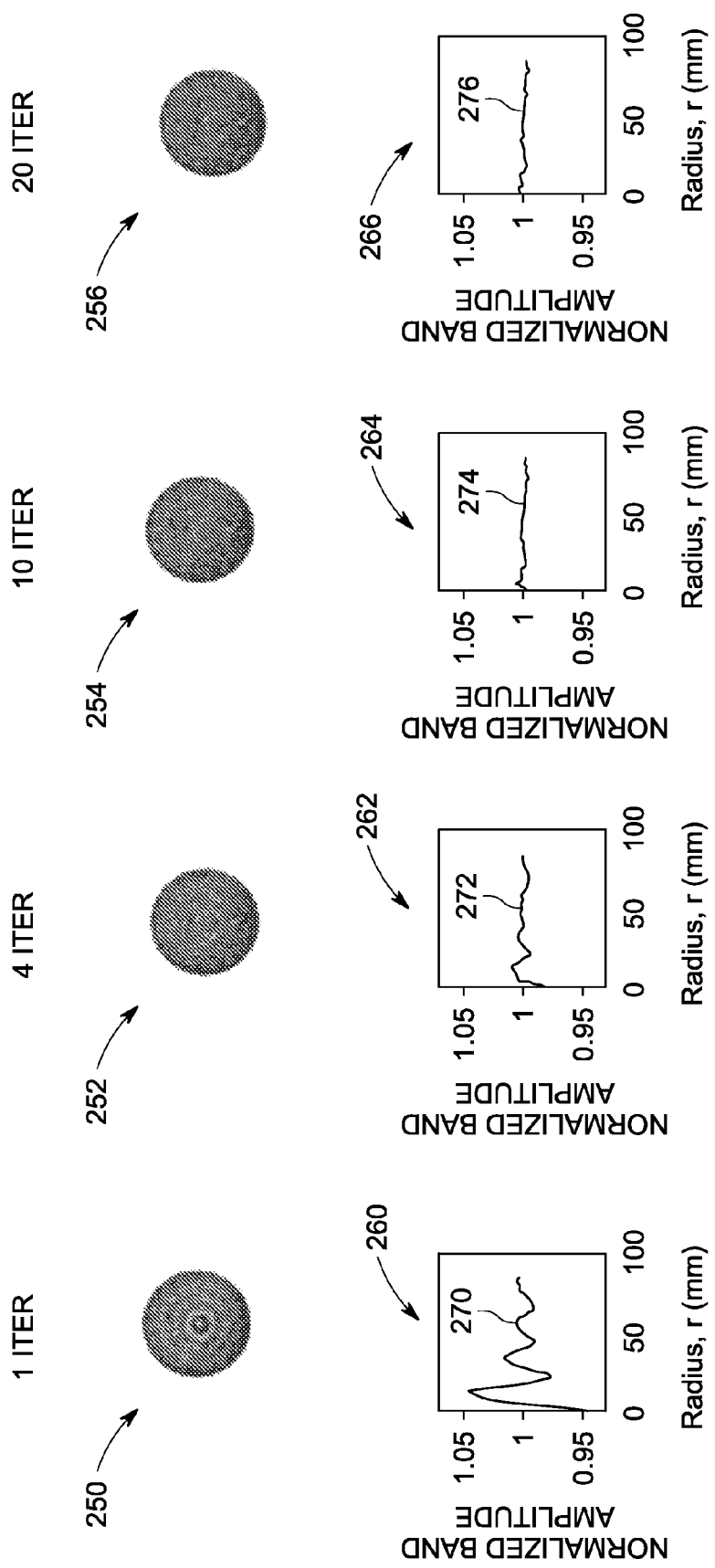
FIG. 6 is a diagram illustrating a reduction in image banding using the method of FIG. 1 and corresponding normalized band amplitude plots.

Accordingly, as shown in FIG. 6, using the method 50, and in particular, as the iterative process is repeated, the reconstructed images approach and appear more like the reference image(s) 186 (as shown in FIG. 3), such that banding and/or artifacts are reduced or eliminated. As can be seen in FIG. 6, the banding and/or artifacts are further reduced after each iteration or plurality of iterations. The reconstructed images 250, 252, 254 and 256 visually illustrate that the banding decreases as the number of iterations of the method 50 increases, and the corresponding geometric calibration improvement increases. The images 250, 252, 254 and 256 illustrate reconstructed images generated using geometric calibration coefficients after one, four, ten and twenty iterations, respectively, of the method 50. Moreover, the reduction in banding is also apparent from the graphs 260, 262, 264 and 266 showing corresponding plots 270, 272, 274 and 276 of normalized band amplitude versus radius for each of the reconstructed images 250, 252, 254 and 256, respectively.

It should be noted that the various embodiments, including the method 50 may be performed using uniform flood scan data from multiple PET scanners or imaging systems with the same geometry. The updated geometric calibrations from each may then be averaged, namely the determined geometric calibration coefficients for each PET scanner is averaged, to determine a final geometric calibration, for example, for a particular type or model of PET scanner having the same geometric design. However, in some embodiments, the methods may be implemented in connection with each PET scanner or imaging system and performed as desired or needed. For example, the method 50 may be performed to generate a customized set of geometric calibration coefficients that are then stored locally in the PET scanner or imaging system. Accordingly, the various embodiments may account for differences between scanners of the same geometric design or configuration by calculating and storing the geometric calibration coefficients for a particular PET scanner or imaging system. The various embodiments also may be used as part of the development of geometric calibrations that are provided in, for example, service packs or system upgrades to installed-base systems.

In the localized calibration process, the various embodiments may be performed, for example, as part of the manufacturing process, during field calibration, during regular system calibration procedures, etc. to provide consistent geometric calibration accuracy. The localized calibration using the various embodiments can account, for example, for mechanical and material differences between PET scanners or imaging systems of the same geometric design.

Thus, the various embodiments may be implemented to provide system-wide or system-specific geometric calibration correction or compensation that account for the geometric properties of the detector system using image-based feedback. For example, the angle between two detector faces can affect the number of coincidence emissions measured. Additionally, and for example, the physical design and alignment of the detector blocks present small geometric differences, such as the location of a crystal within the crystal block. The various embodiments may be provided as part of a process to determine and create geometric calibration coefficients for PET scanners or imaging systems. According to various embodiments, banding artifacts and quantitation inconsistencies in the center of an image are reduced. In some embodiments, the iterative methods described herein evaluate banding rings in the image space and correct or compensate for the banding rings in the projection space.

The geometric calibration coefficients may be used to obtain normalization factors for PET normalization for image reconstruction, for example, as described in U.S. Pat. No. 5,543,622. As described there three-dimensional (3D) normalization for PET may be performed with (1) geometric calibration factors computed for a transmission rod scan and (2) crystal efficiency factors computed from a flood phantom scan. It should be noted that the various embodiments are not limited to the use of a rod scan for determining the geometric factors, but instead can be obtained from simulation or other source distribution.

Modifications and variations to the various embodiments are contemplated. For example, the number of iterations of the methods described herein or the convergence criteria may be varied. In some embodiments, a damping coefficient can be used when updating the geometric calibration coefficients, which may increase stability. Additionally, varying levels of smoothing can be performed on the reconstructed images, which may improve performance or decrease susceptibility to noise. The updates to the geometric calibrations may be windowed to reduce the likelihood of or prevent abrupt changes during each geometric calibration update, during the final geometric calibration (by combining in a windowed manner with the original geometric calibration), or both. The images also may be windowed about the center of the PET gantry before forward projection, which reduces potential problems at the phantom edge boundary during reconstruction. The reference image(s) may be regenerated with the updated geometric calibration after a predetermined number of iterations of the methods described herein.

Additionally, although some embodiments are described in connection with using a centered flood phantom to provide for the removal of the "rings" or "bands" that can occur in images, variations are contemplated. For example, the various embodiments may be implemented in connection with a flood phantom (or other calibration source) that is positioned off-center within the bore of the imaging system, such as raised up and/or down or moved left or right. In particular, as an activity source is displaced from the center (e.g., of the imaging bore), gradual (low-frequency) variations can lead to undesired activity measurement variation in the image. These variations are also a result of an inaccurate geometric calibration. Accordingly, these low-frequency variations causing variations in images can be reduced or eliminated in accordance with the various embodiments described herein an using an off-center phantom. By adjusting the position of, for example, the uniform flood phantom, and modifying the geometric calibration based on the activity of the flood phantom at each location, the low-frequency variation can be reduced or eliminated.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for providing geometric calibration for a positron emission tomography (PET) imaging system, the method comprising:
   obtaining scan data for a uniform phantom;
   generating reference images based on the scan data for the uniform phantom;
   reconstructing images of the uniform phantom using a PET imaging system; and
   determining a geometric calibration for the PET imaging system based on a comparison of the reconstructed images and the reference images.

2. A method in accordance with claim 1 wherein generating the reference images comprises removing bands from reconstructed images of the uniform phantom to generate the reference images based on a known distribution activity of the uniform phantom.

3. A method in accordance with claim 1 wherein generating the reference images comprises removing image artifacts from reconstructed images of the uniform phantom to generate the reference images based on a known distribution activity of the uniform phantom.

4. A method in accordance with claim 1 further comprising forward projecting the reference images and the reconstructed images to use in the comparison.

5. A method in accordance with claim 1 further comprising determining a ratio based on the comparison of the reconstructed images and the reference images.

6. A method in accordance with claim 1 further comprising updating the geometric calibration iteratively based on a plurality of comparisons of the reconstructed images and the reference images.

7. A method in accordance with claim 6 further comprising determining whether a predetermined convergence is satisfied with respect to the comparisons and providing a final geometric calibration when the convergence is satisfied.

8. A method in accordance with claim 1 wherein determining the geometric calibration is performed for a single PET imaging system.

9. A method in accordance with claim 1 wherein determining the geometric calibration is performed for a plurality of PET imaging systems and further comprising determining a PET system geometric calibration based on the plurality of geometric calibrations.

10. A method in accordance with claim 9 further comprising determining an average of the plurality of geometric calibrations as the PET system geometric calibration.

11. A method in accordance with claim 1 wherein the uniform phantom comprises a uniform cylindrical flood phantom.

12. A method in accordance with claim 1 further comprising performing a low order least squares fit to generate the reference images.

13. A method in accordance with claim 1 further comprising performing a windowing process on the reconstructed images before determining the geometric calibration.

14. A method in accordance with claim 1 further comprising iteratively determining the geometric calibration based on a plurality of comparisons between the reference images and reconstructed images, wherein a seed geometric calibration is used for a first iteration.

15. A method in accordance with claim 1 further wherein the uniform phantom positioned centrally within a bore of the PET imaging system.

16. A method in accordance with claim 1 further wherein the uniform phantom positioned off-center within a bore of the PET imaging system.

17. A non-transitory computer readable medium for calibrating a positron emission tomography (PET) imaging system, the computer readable medium being programmed to instruct a computer to:
   generate artifact reduced PET reference images based on a priori information of a scanned uniform phantom; and
   determine a geometric calibration for the PET imaging system using an image-domain based iterative calibration determination process with image-based feedback from the reference images.

18. A non-transitory computer readable medium in accordance with claim 17 wherein the program further instructs the computer to reconstruct images using the PET imaging system and forward project the reference images and the reconstructed images to perform a comparison for determining the geometric calibration.

19. A non-transitory computer readable medium in accordance with claim 17 wherein the program further instructs the computer to determine a geometric calibration for a plurality of PET imaging systems and average values from the geometric calibrations to determine a system geometric calibration.

20. A non-transitory computer readable medium in accordance with claim 17 wherein the program further instructs the computer to perform the iterative calibration determination process until a predetermined convergence level is reached.

21. A positron emission tomography (PET) imaging system comprising:
   a gantry;
   a detector ring mounted to the gantry, the detector ring having a plurality of detector elements; and
   a geometric calibration determination module configured to generate reconstructed images of a uniform phantom imaged by the plurality of detector elements to create a plurality of reference images used in an iterative image-based feedback process and to determine a geometric calibration for the imaging detectors.

22. A PET imaging system in accordance with claim 21 wherein the geometric calibration determination module is configured to generate band free reconstructed images based on the uniform phantom and that define the reference images.

* * * * *